United States Patent [19]

van Erp et al.

[11] Patent Number: 4,637,993

[45] Date of Patent: Jan. 20, 1987

[54] PROCESS FOR PREPARATION OF CATALYST

[75] Inventors: Willibrord A. van Erp; Johannes M. Nanne; Martin F. M. Post, all of Amsterdam, Netherlands

[73] Assignee: Shell Oil Company, Houston, Tex.

[21] Appl. No.: 780,066

[22] Filed: Sep. 25, 1985

[30] Foreign Application Priority Data

Oct. 4, 1984 [NL] Netherlands .......................... 8403021

[51] Int. Cl.$^4$ ........................ B01J 21/06; B01J 21/08; B01J 23/74
[52] U.S. Cl. .................................... 502/242; 518/718
[58] Field of Search .............. 502/242, 260, 325, 332; 518/715

[56] References Cited

U.S. PATENT DOCUMENTS

| | | | |
|---|---|---|---|
| 4,499,209 | 2/1985 | Hoek et al. | 502/242 X |
| 4,522,939 | 6/1985 | Minderhoud et al. | 502/242 |

FOREIGN PATENT DOCUMENTS

| | | | |
|---|---|---|---|
| 2092172 | 8/1982 | United Kingdom | 518/715 |
| 2130601 | 6/1984 | United Kingdom | 518/715 |

Primary Examiner—W. J. Shine

[57] ABSTRACT

Supported cobalt catalysts with specified inhomogeneous cobalt distribution over the catalyst particles (expressed as a ratio $(\Sigma V_p/\Sigma V_c) \leq 0.55$ are prepared by immersion of a porous carrier into a solution of a cobalt compound in such a way that a given relation between the viscosity (in cS) and Temperature (degrees K.) of the solution and the immersion time (in sec) is met. For each immersion, this relation is $(\log v/t \times T) \times 10^4 \geq 1$.

4 Claims, No Drawings

PROCESS FOR PREPARATION OF CATALYST

FIELD OF THE INVENTION

The invention relates to a process for the preparation of catalysts comprising cobalt supported on a carrier as well as the use of these catalysts in the preparation of hydrocarbons from mixtures of carbon monoxide and hydrogen.

BACKGROUND OF THE INVENTION

The preparation of hydrocarbons from a $H_2/CO$ mixture by contacting this mixture at elevated temperature and pressure with a catalyst is known in the literature as the Fischer-Tropch hydrocarbon synthesis. Catalysts suitable for this purpose are catalysts comprising cobalt supported on a carrier. Such catalysts can be prepared by contacting particles of a porous carrier for a considerable period of time with a solution of a cobalt compound, subsequently removing the solvent and calcining and activating the composition obtained. In this manner are generally obtained catalyst particles in which the cobalt is distributed homogeneously over the carrier material, viz. at each point of the catalyst particle the cobalt concentration present is virtually the same.

An investigation into the use of catalysts comprising cobalt supported on a carrier for the preparation of hydrocarbons from $H_2/CO$ mixtures has recently shown that catalysts in which the cobalt is inhomogeneously distributed over the carrier material show a higher $C_5+$ selectivity than similar catalysts in which the cobalt is distributed homogeneously over the carrier, provided that said inhomogeneous distribution meets certain requirements. In order to assess the inhomogeneity of the cobalt distribution over the catalyst particles, the latter are regarded as being composed or a kernel surrounded by a peel, the kernel being of such a shape that at every point of the kernel perimeter the shortest distance (d) to the perimeter of the peel is the same and that d is equal to all catalyst particles under consideration and has been chosen such that the quantity of cobalt present in the total peel volume $(\Sigma V_p)$ is 90% of the quantity of cobalt present in the total volume of the catalyst particles under consideration $(\Sigma V_c)$. For determining $\Sigma V_p$, the "electron microprobe analysis" method can very suitably be used. It was found that the catalysts having an inhomogeneous cobalt distribution show no significant improvement in $C_5+$ selectivity relative to catalysts with homogeneous cobalt distribution, unless the inhomogeneous cobalt distribution is such as to meet the requirement $(\Sigma V_p/\Sigma V_c) < 0.85$. Since the investigation has further shown that the catalysts have higher $C_5+$ selectivities according as their $(\Sigma V_p/\Sigma V_c)$ quotients are lower, the preferred catalysts for use on a technical scale are those having low $(\Sigma V_p/\Sigma V_c)$ quotients, and in particular those having quotients $(\Sigma V_p/\Sigma V_c) \leq 0.55$.

The present patent application relates to a process for the preparation of such catalysts by immersing a porous carrier once or several times in a solution of a cobalt compound, removing the liquid from the composition after each immersion and finally calcining and activating the composition. It has been found that the quotient $(\Sigma V_p/\Sigma V_c)$ of the catalysts prepared in this manner is largely dependent on the viscosity measured at 60° C. (v in cS) and the temperature (T in °K.) of the solution, and the immersion time (t in seconds), and that in order to prepare catalysts having a quotient $(\Sigma V_p/\Sigma V_c) \leq 0.55$, during the immersion the following relation between v, T and t should be satisfied: (log $v/t \times T) \times 10^4 \geq 1$.

SUMMARY OF THE INVENTION

The present patent application therefore relates to a process for the preparation of catalysts comprising cobalt supported on a carrier, wherein catalysts in which the cobalt is distributed over the carrier in such a manner as to satisfy the relation $(\Sigma V_p/\Sigma V_c) \leq 0.55$ are prepared by immersing a porous carrier once or several times in a solution of a cobalt compound, removing the liquid from the composition after each immersion and finally calcining and activating the composition, wherein during each immersion the following relation between the viscosity measured at about 60° C. (v in cS) and the temperature (T in °K.) of the solution, and the immersion time (t in seconds) is satisfied: (log $v/t \times T) \times 10^4 \geq 1$, and wherein $\Sigma V_p$ and $\Sigma V_c$ have the meanings mentioned hereinbefore.

The patent application further relates to the use of the catalysts prepared in this manner for the preparation of hydrocarbons from mixtures of carbon monoxide and hydrogen.

DESCRIPTION OF THE PREFERRED EMBODIMENTS

In the process according to the invention, the porous carrier should be immersed once or several times in a solution of a cobalt compound. Suitable for the purpose are both solutions of cobalt compounds in water, to which optionally a thickener, such as hydroxyethylcellulose, may be added, and solutions of cobalt compounds in organic solvents, such as ethanol or glycol.

The catalysts prepared according to the invention contain cobalt supported on a porous carrier. Very suitable carriers are, inter alia, silica, alumina and silica-alumina. Preference is given to the use of silica as carrier. The quantities of cobalt present on the catalysts may vary within wide ranges. Preference is given to the preparation of catalysts comprising about 3–60, and in particular about 5–50, parts by weight of cobalt per 100 parts by weight of carrier material. The catalysts prepared according to the invention preferably include one or more promoters. Suitable promoters for the present cobalt catalysts are iron, magnesium, zinc and thorium. It is preferred to prepare catalysts which include zirconium, titanium, chromium or ruthenium as promoter. Special preference is given to the use of zirconium as promoter. The preferred quantities of promoter present in the cobalt catalysts are dependent on the way in which the promoter has been deposited. In the case of catalysts prepared by depositing the cobalt on the carrier first, and then the promoter, preference is given to catalysts comprising about 0.1–5 parts by weight of the promoter per 100 parts by weight of carrier. In the case of catalysts prepared by depositing the promoter on the carrier first, and then the cobalt, preference is given to catalysts comprising about 5–40 parts by weight of the promoter per 100 parts by weight of carrier.

A correct inhomogeneous distribution of the cobalt over the carrier is essential to the catalysts according to the invention. If, in addition to cobalt, the catalyst includes a promoter, such as zirconium, the latter may be distributed over the carrier either homogeneously or inhomogeneously. Homogeneous distribution of the promoter will occur when the promoter is deposited on the carrier by way of conventional impregnation, either preceding or following the deposition of the cobalt on the carrier. Inhomogeneous distribution of the promoter may occur when the cobalt and the promoter are deposited simultaneously by immersing the porous carrier in a solution comprising both a cobalt compound and a compound of the promoter.

The present patent application also relates to the use of the catalysts prepared according to the invention for the conversion of a $H_2/CO$ mixture into hydrocarbons. Before becoming eligible for this use, the cobalt catalysts should be activated. This activation can suitably be carried out by contacting the catalysts at a temperature between 200° and 350° C. with hydrogen or a hydrogen-containing gas.

The conversion of a $H_2/CO$ mixture into hydrocarbons by using a catalyst according to the invention is preferably carried out at a temperature of about 125°–350° C. and in particular of about 175°–275° C. and a pressure of about 5–100 bar and in particular of about 10–75 bar. Further, the conversion is preferably carried out by contacting the $H_2/CO$ mixture with a catalyst which is present in the form of a fixed bed having an external surface area ($S_E$) between about 5 and about 70 cm$^2$/ml. In this case, it is particularly preferred to use a catalyst wherein $(\Sigma V_p/\Sigma V_c) > 0.03 \times \sqrt{S_E}$.

$H_2/CO$ mixtures which are eligible to be converted according to the invention into hydrocarbons can very suitably be obtained by steam reforming or partial oxidation starting from light hydrocarbons, such as natural gas.

The $H_2/CO$ mixture which is converted according to the invention into hydrocarbons preferably has a $H_2/CO$ molar ratio higher than about 1.5. If the feed has a $H_2/CO$ molar ratio lower than about 1.5, it is preferred to increase the latter to a value lying between about 1.5 and about 2.5 and in particular between about 1.75 and about 2.25, before the feed is contacted with the cobalt catalyst. The $H_2/CO$ molar ratio of hydrogen-poor $H_2/CO$ mixtures can be increased, inter alia by addition of hydrogen, removal of carbon monoxide, mixing with a hydrogen-rich $H_2/CO$ mixture or by subjecting the hydrogen-poor $H_2/CO$ mixture to the CO-shift reaction.

The conversion of the $H_2/CO$ mixture according to the invention can suitably be used as an independent process in which unconverted synthesis gas can be recirculated, if desired. The conversion of the $H_2/CO$ mixture according to the invention can also very suitably be used as the first step in a two-step process for the preparation of middle distillates from $H_2/CO$ mixtures. For it has been found that catalysts containing silica, alumina or silica-alumina as carrier and cobalt together with zirconium, titanium, chromium and/or ruthenium as catalytically active metals, which catalysts have been prepared by depositing the metals concerned on the carrier material by impregnation, yield a product substantially consisting of unbranched paraffins the high-boiling part of which can be converted in high yield into middle distillates by subjecting it to a hydrocracking treatment.

Although in the preparation of middle distillates from the product obtained over the cobalt catalyst the part of the product whose initial boiling point lies above the final boiling point of the heaviest middle distillate desired as end product will do as feed for the hydrocracking, the total $C_5+$ fraction of the product prepared over the cobalt catalyst may also be used for the purpose, if desired.

The hydrocracking is carried out by contacting the fraction to be treated at elevated temperature and pressure and in the presence of hydrogen with a catalyst comprising one or more Group VIII noble metals on a carrier. The hydrocracking catalyst used by preference is a catalyst comprising about 0.2–1 %w of platinum or palladium supported on silica-alumina as carrier. The hydrocracking treatment is preferably carried out at a temperature of about 250°–350° C. and a pressure of about 10–75 bar.

The invention is now illustrated with the aid of the following example which is not intended to be construed as limiting the invention.

EXAMPLE

Catalyst preparation

Fourteen Co/Zr/SiO$_2$ catalysts (catalysts 1–14) were prepared as follows, starting from a spherical silica carrier dried at 120° C.

Catalyst 1

The silica carrier was contacted at a temperature of 20° C. for 15 minutes with a solution of cobalt nitrate in water. The quantity of solution used was such that its volume corresponded substantially with the pore volume of the carrier. The solution had a viscosity, measured at 60° C., of 1.7 cS. After drying and calcining at 500° C., the cobalt-loaded carrier was kept in contact with a solution of zirconium nitrate in water. Again, the quantity of solution used was of such a volume as to correspond substantially with the pore volume of the carrier. Finally the cobalt- and zirconium-loaded carrier was dried and calcined at 500° C.

Catalyst 2

The silica carrier was kept immersed in water of 20° C. for 30 minutes. After dripdrying, the water-saturated carrier was immersed three times—each time for 30 seconds—at a temperature of 20° C. in the same solution of cobalt nitrate in water as was used in the preparation of catalyst 1. After each immersion, the material was dried and calcined at 500° C. Subsequently, zirconium was deposited on the cobalt-loaded carrier in a way identical to that described for the preparation of catalyst 1.

Catalyst 3

This catalyst was prepared in substantially the same way as catalyst 2, the difference being that in the present case four immersions in the cobalt nitrate solution were performed.

Catalysts 4–14

These catalysts were prepared by immersing the silica carrier once or several times—each time for t seconds—in a solution of cobalt nitrate in a solvent. After each immersion, the material was dried and calcined at 500° C. Subsequently zirconium was deposited on the cobalt-loaded carriers in a way identical to that described for the preparation of catalyst 1.

Further information on catalysts 4–14, which, like catalysts 1–3, comprise 0.9 g of Zr per 100 g of SiO$_2$, is given in Table I.

Catalyst testing

Catalysts 1–3, 5, 7 and 11 were used in six experiments (experiments 1–6) in the preparation of hydrocarbons from a mixture of carbon monoxide and hydrogen having a $H_2/CO$ molar ratio 2. The experiments were carried out at a pressure of 20 bar and a space velocity of 600 Nl.l$^{-1}$.h$^{-1}$ in a reactor containing a fixed catalyst bed having an $S_E$ of 13 cm$^2$/ml. Preceding the testing, the catalysts were activated by subjection to a hydrotreatment at 250° C. Further information on experiments 1–6 is given in Table II.

Of the catalysts mentioned in Table I, only catalysts 4, 5, 7, 11, 12 and 14, where $(\Sigma V_p/\Sigma V_c)<0.55$, are catalysts according to the invention. In the preparation of these catalysts, the requirement (log v/t×T)×10$^4$ ≧ 1 was satisfied. Catalysts 1–3, 6, 8–10 and 13, where $(\Sigma V_p/\Sigma V_c)>0.55$, fall outside the scope of the invention. They have been included in the patent application for comparison. In the preparation of catalysts 1, 6, 8–10 and 13, the requirement (log v/t×T)×10$^4$ ≧ 1 was not satisfied. In the preparation of catalysts 2 and 3 the cobalt was deposited on a water-saturated carrier. Furthermore, in the preparation of catalysts 2 and 3 the requirement (log v/t×T)×10$^4$ ≧ 1 was not satisfied.

Of the experiments mentioned in Table II, only experiments 4–6 are experiments according to the invention. In these experiments, which were carried out by using catalysts where $(\Sigma V_p/\Sigma V_c)<0.55$, very high $C_5^+$ selectivities were observed. Experiments 1–3 fall outside the scope of the invention. They have been included in the patent application for comparison. In these experiments, which were carried out by using catalysts where $(\Sigma V_p/\Sigma V_c)>0.55$, considerably lower $C_5^+$ selectivities were attained.

We claim as our invention:

1. A process for the preparation of catalysts comprising cobalt and a zirconium promoter supported on a silica carrier, wherein the cobalt is distributed over the carrier in such a manner as to satisfy the relation $(\Sigma V_p/\Sigma V_c) \leq 0.55$, where $\Sigma V_c$ represents the total volume of the catalysts particles under consideration and $\Sigma V_p$ is found by adding up the peel volumes present in the catalyst particles, the latter being regarded as being composed of a kernel surrounded by a peel, which kernel is of such a shape that at every point of the kernel perimeter the shortest distance (d) to the perimeter of the peel is the same, d being equal for all catalyst particles under consideration, and having been chosen such that the quantity of cobalt present in $\Sigma V_p$ is 90% of the quantity of cobalt present in $\Sigma V_c$, which process comprises immersing a porous carrier once or several times in a solution of a cobalt compound, removing the liquid from the composition after each immersion and finally calcining and activating the composition, that during each immersion the following relation between the viscosity measured at 60° C. (v in cS) and the temperature (T in °K.) of the solution, and the immersion time (t in s) is satisfied: (log v/t×T)×10$^4$ ≧ 1.

2. The process of claim 1 wherein the catalyst comprises 3–60 parts by weight of cobalt per 100 parts by weight of carrier.

3. The process of claim 2 wherein the catalyst comprises 5–50 parts by weight of cobalt per 100 parts by weight of carrier.

4. The process of claim 1 wherein per 100 parts by weight of carrier the catalyst includes either 0.1–5 parts by weight of promoter, if during the preparation the cobalt was deposited first and the promoter next, or 5–40 parts by weight of promoter, if during the preparation the promoter was deposited first and the cobalt next.

TABLE I

| Cat. No. | Co in Present In Solvent, % w | Solvent | t, s | T, °K. | v, cS | Number Of Immersion Steps | Cobalt Load, g Co/100 g SiO$_2$ | $\frac{\log v}{t \times T} \times 10^4$ | $\frac{\Sigma V_p}{\Sigma V_c}$ |
|---|---|---|---|---|---|---|---|---|---|
| 4 | 15 | ethanol | 5 | 301 | 7.3 | 2 | 10 | 5.7 | 0.40 |
| 5 | 15 | " | 15 | 301 | 7.3 | 2 | 12 | 1.9 | 0.45 |
| 6 | 15 | " | 120 | 301 | 7.3 | 2 | 17 | 0.2 | 0.75 |
| 7 | 17 | " | 15 | 313 | 9.1 | 1 | 9 | 2.0 | 0.40 |
| 8 | 10 | water | 15 | 293 | 0.9 | 3 | 10 | −0.1 | 0.75 |
| 9 | 15 | " | 30 | 293 | 1.7 | 2 | 16 | 0.3 | 0.75 |
| 10 | 15 | " | 60 | 293 | 1.7 | 1 | 11 | 0.1 | 0.85 |
| 11 | 19 | " | 5 | 328 | 5.8 | 2 | 10 | 4.7 | 0.45 |
| 12 | 15 | glycol | 30 | 293 | 11.8 | 2 | 21 | 1.2 | 0.50 |
| 13 | 14 | water + HEC* | 75 | 318 | 9.6 | 1 | 19 | 0.4 | 0.75 |
| 14 | 14 | " | 30 | 293 | 9.6 | 1 | 9 | 1.1 | 0.45 |

*HEC = hydroxyethylcellulose in a 0.5-% w concentration

TABLE II

| Experiment No. | 1 | 2 | 3 | 4 | 5 | 6 |
|---|---|---|---|---|---|---|
| Catalyst No. | 1 | 2 | 3 | 5 | 7 | 11 |
| Cobalt load, g Co/100 g SiO$_2$ | 22 | 18 | 22 | 12 | 9 | 10 |
| $\frac{\Sigma V_p}{\Sigma V_c}$ | 0.88 | 0.75 | 0.73 | 0.45 | 0.40 | 0.45 |
| Temperature during synthesis gas conversion, °C. | 230 | 235 | 225 | 220 | 220 | 220 |
| Nl synthesis gas converted per g Co per hour | 5.1 | 7.4 | 5.8 | 8.6 | 10.1 | 6.8 |
| $C_5^+$ selectivity, % w | 59 | 65 | 66 | 76 | 74 | 75 |